United States Patent
Kaminsky

(10) Patent No.: US 7,026,492 B1
(45) Date of Patent: Apr. 11, 2006

(54) DIRECT EPOXIDATION PROCESS USING MODIFIERS

(75) Inventor: Mark P. Kaminsky, Media, PA (US)

(73) Assignee: Lyondell Chemical Technology, L.P., Greenville, DE (US)

( * ) Notice: Subject to any disclaimer, the term of this patent is extended or adjusted under 35 U.S.C. 154(b) by 0 days.

(21) Appl. No.: 10/977,444

(22) Filed: Oct. 29, 2004

(51) Int. Cl.
*C07D 301/06* (2006.01)
*C07D 301/08* (2006.01)
*C07D 301/04* (2006.01)
*C07D 301/10* (2006.01)

(52) U.S. Cl. ............... 549/523; 549/533; 549/536
(58) Field of Classification Search ........... 549/533, 549/523, 536
See application file for complete search history.

(56) References Cited

U.S. PATENT DOCUMENTS

| | | | |
|---|---|---|---|
| 3,351,635 A | 11/1967 | Kollar | 260/348.5 |
| 4,367,342 A | 1/1983 | Wulff et al. | 549/529 |
| 4,410,501 A | 10/1983 | Taramasso et al. | 423/326 |
| 4,833,260 A | 5/1989 | Neri et al. | 549/531 |
| 5,859,265 A | 1/1999 | Muller et al. | 549/531 |
| 6,005,123 A | 12/1999 | Dessau et al. | 549/531 |
| 6,008,388 A | 12/1999 | Dessau et al. | 549/531 |
| 6,348,607 B1 * | 2/2002 | Muller et al. | 549/523 |
| 6,399,794 B1 | 6/2002 | Hancu | 549/533 |
| 6,555,493 B1 | 4/2003 | Cooker et al. | 504/74 |

FOREIGN PATENT DOCUMENTS

| | | |
|---|---|---|
| BE | 1001038 A7 | 6/1989 |
| EP | 916403 A2 * | 5/1999 |
| JP | 4-352771 | 12/1992 |
| WO | 98/00413 | 1/1998 |

* cited by examiner

*Primary Examiner*—Bernard Dentz
(74) *Attorney, Agent, or Firm*—Kevin M. Carroll

(57) ABSTRACT

The invention is a process for epoxidizing an olefin with hydrogen and oxygen in the presence of a noble metal-containing titanium or vanadium zeolite and a modifier selected from the group consisting of carbon monoxide, methylacetylene, and propadiene. The process results in significantly reduced alkane by-product formed by the hydrogenation of olefin compared to processes that do not use the carbon monoxide, methylacetylene, and/or propadiene modifier.

16 Claims, No Drawings

DIRECT EPOXIDATION PROCESS USING MODIFIERS

FIELD OF THE INVENTION

This invention relates to an epoxidation process which comprises reacting olefin, hydrogen, and oxygen in the presence of a noble metal-containing titanium or vanadium zeolite catalyst and a modifier selected from the group consisting of carbon monoxide, methylacetylene, and/or propadiene. Surprisingly, the process results in lower selectivity to undesired alkane byproduct formed by the hydrogenation of olefin compared to processes without the modifier.

BACKGROUND OF THE INVENTION

Many different methods for the preparation of epoxides have been developed. Generally, epoxides are formed by the reaction of an olefin with an oxidizing agent in the presence of a catalyst. The production of propylene oxide from propylene and an organic hydroperoxide oxidizing agent, such as ethyl benzene hydroperoxide or tert-butyl hydroperoxide, is commercially practiced technology. This process is performed in the presence of a solubilized molybdenum catalyst, see U.S. Pat. No. 3,351,635, or a heterogeneous titania on silica catalyst, see U.S. Pat. No. 4,367,342. Another commercially practiced technology is the direct epoxidation of ethylene to ethylene oxide by reaction with oxygen over a silver catalyst. Unfortunately, the silver catalyst has not proved useful in commercial epoxidation of higher olefins.

Besides oxygen and alkyl hydroperoxides, another oxidizing agent useful for the preparation of epoxides is hydrogen peroxide. U.S. Pat. No. 4,833,260, for example, discloses the epoxidation of olefins with hydrogen peroxide in the presence of a titanium silicate catalyst.

Much current research is conducted in the direct epoxidation of olefins with oxygen and hydrogen. In this process, it is believed that oxygen and hydrogen react in situ to form an oxidizing agent. Many different catalysts have been proposed for use in the direct epoxidation of higher olefins. Typically, the catalyst comprises a noble metal that is supported on a titanosilicate. For example, JP 4-352771 discloses the formation of propylene oxide from propylene, oxygen, and hydrogen using a catalyst containing a Group VIII metal such as palladium on a crystalline titanosilicate. The Group VIII metal is believed to promote the reaction of oxygen and hydrogen to form an in situ oxidizing agent. U.S. Pat. No. 5,859,265 discloses a catalyst in which a platinum metal, selected from Ru, Rh, Pd, Os, Ir and Pt, is supported on a titanium or vanadium silicalite. Other direct epoxidation catalyst examples include gold supported on titanosilicates, see for example PCT Intl. Appl. WO 98/00413.

One disadvantage of the described direct epoxidation catalysts is that they are prone to produce non-selective by-products such as glycols or glycol ethers formed by the ring-opening of the epoxide product or alkane by-product formed by the hydrogenation of olefin. U.S. Pat. No. 6,008,388 describes a direct olefin epoxidation process in which the selectivity for the reaction of olefin, oxygen, and hydrogen in the presence of a noble metal-modified titanium zeolite is enhanced by the addition of a nitrogen compound such as ammonium hydroxide to the reaction mixture. U.S. Pat. No. 6,399,794 teaches the use of ammonium bicarbonate modifiers to decrease the production of ring-opened by-products. U.S. Pat. No. 6,005,123 teaches the use of phosphorus, sulfur, selenium or arsenic modifiers such as benzothiophene to decrease the production of propane.

As with any chemical process, it is desirable to attain still further improvements in the epoxidation methods and catalysts. We have discovered an effective, convenient process to form an epoxidation catalyst and its use in the epoxidation of olefins.

SUMMARY OF THE INVENTION

The invention is an olefin epoxidation process that comprises reacting olefin, oxygen, and hydrogen in the presence of a noble metal-containing titanium or vanadium zeolite catalyst and a modifier selected from the group consisting of carbon monoxide, methylacetylene, and propadiene. This process surprisingly gives significantly reduced alkane by-product formed by the hydrogenation of olefin compared to processes that do not use the modifier.

DETAILED DESCRIPTION OF THE INVENTION

The process of the invention employs a noble metal-containing titanium or vanadium zeolite catalysts. Noble metal-containing titanium or vanadium zeolite catalysts are well known in the art and are described, for example, in JP 4-352771 and U.S. Pat. Nos. 5,859,265 and 6,555,493, the teachings of which are incorporated herein by reference in their entirety. Such catalysts typically comprise a titanium or vanadium zeolite and a noble metal, such as palladium, gold, platinum, silver, iridium, ruthenium, osmium, or combinations thereof. The catalysts may contain a mixture of noble metals. Preferred catalysts comprise palladium and a titanium or vanadium zeolite, palladium, gold, and a titanium or vanadium zeolite, or palladium, platinum, and titanium or vanadium zeolite.

Titanium or vanadium zeolites comprise the class of zeolitic substances wherein titanium or vanadium atoms are substituted for a portion of the silicon atoms in the lattice framework of a molecular sieve. Such substances are well known in the art. Particularly preferred titanium zeolites include the class of molecular sieves commonly referred to as titanium silicalites, particularly "TS-1" (having an MFI topology analogous to that of the ZSM-5 aluminosilicate zeolites), "TS-2" (having an MEL topology analogous to that of the ZSM-11 aluminosilicate zeolites), and "TS-3" (as described in Belgian Pat. No. 1,001,038). Titanium-containing molecular sieves having framework structures isomorphous to zeolite beta, mordenite, ZSM48, ZSM-12, MCM-22(MWW), and MCM-41 are also suitable for use. The titanium zeolites preferably contain no elements other than titanium, silicon, and oxygen in the lattice framework, although minor amounts of boron, iron, aluminum, sodium, potassium, copper and the like may be present.

The typical amount of noble metal present in the noble metal-containing titanium or vanadium zeolite will be in the range of from about 0.001 to 20 weight percent, preferably 0.005 to 10 weight percent, and particularly 0.01 to 5 weight percent. The manner in which the noble metal is incorporated into the catalyst is not considered to be particularly critical. For example, the noble metal may be supported on the zeolite by impregnation or the like. Alternatively, the noble metal can be incorporated into the zeolite by ion-exchange with, for example, tetraammine palladium dichloride.

There are no particular restrictions regarding the choice of noble metal compound used as the source of noble metal. For example, suitable compounds include the nitrates, sulfates, halides (e.g., chlorides, bromides), carboxylates (e.g. acetate), and amine complexes of the noble metal. The noble metal may be in an oxidation state anywhere from 0 to +4 or any combination of such oxidation states. To achieve the desired oxidation state or combination of oxidation states, the noble metal compound may be calcined, reduced, or a combination thereof. Satisfactory catalytic performance can, however, be attained without any pre-reduction. To achieve the active state of noble metal, the noble metal-containing titanium or vanadium zeolite may undergo pretreatment such as thermal treatment in nitrogen, vacuum, hydrogen, or air.

The noble metal-containing titanium or vanadium zeolite catalyst may also comprise a mixture of palladium-containing titanium or vanadium zeolite and palladium-free titanium or vanadium zeolite. The palladium-free titanium or vanadium zeolite is a titanium or vanadium-containing molecular sieve that is free of added palladium. The addition of a palladium-free titanium or vanadium zeolite has proven beneficial to productivity of the palladium that is present in the catalyst.

The noble metal-containing titanium or vanadium zeolite catalyst may be used in the epoxidation process as a powder or as a large particle size solid. Preferably, the noble metal-containing titanium or vanadium zeolite is spray dried, pelletized or extruded prior to use in epoxidation. If spray dried, pelletized or extruded, the catalyst may additionally comprise a binder or the like and may be molded, spray dried, shaped or extruded into any desired form prior to use in epoxidation. The noble metal-containing titanium or vanadium zeolite may also be encapsulated in polymer as described in copending U.S. application Ser. No. 10/796, 680, the teachings of which are incorporated herein by reference in their entirety.

The epoxidation process of the invention also employs one or more modifiers selected from the group consisting of carbon monoxide (CO), methylacetylene (MA), and propadiene (PD).

Sufficient carbon monoxide, methylacetylene, and/or propadiene is necessary to be effective to lower the amount of alkane by-product formed by the hydrogenation to olefin as compared to the same reaction carried out under similar conditions in the absence of modifier. The modifier will typically be added to the reaction mixture along with the other reaction gases, comprising oxygen, hydrogen, and light olefins such as propylene which may be introduced in the gas phase. The amount of modifier in the gas is preferably in the range of from about 0.00001 volume percent (0.1 ppmv) to about 10 volume % (as measure by volume modifier per total volume of all gases introduced into the reactor), and most preferably from about 0.001 volume % to about 5 volume %. If CO is used as modifier, the most preferable amount is from about 0.001 volume % to about 0.005 volume %. Mixtures of CO, MA, or PD may also be used, particularly mixtures of MA and PD. If an MA and PD mixture is used, the most preferred amount of combined MA and PD is from about 0.05 to about 5 volume %. If an MA and PD mixture is used, molar ratios of MA:PD typically range from about 0.01 to about 100.

The epoxidation process of the invention comprises contacting an olefin, oxygen, and hydrogen in the presence of one or more modifier and the catalyst. Suitable olefins include any olefin having at least one carbon—carbon double bond, and generally from 2 to 60 carbon atoms. Preferably the olefin is an acyclic alkene of from 2 to 30 carbon atoms; the process of the invention is particularly suitable for epoxidizing $C_2$–$C_6$ olefins. More than one double bond may be present, as in a diene or triene for example. The olefin may be a hydrocarbon (i.e., contain only carbon and hydrogen atoms) or may contain functional groups such as halide, carboxyl, hydroxyl, ether, carbonyl, cyano, or nitro groups, or the like. The process of the invention is especially useful for converting propylene to propylene oxide.

Oxygen and hydrogen are also required for the epoxidation process. Although any sources of oxygen and hydrogen are suitable, molecular oxygen and molecular hydrogen are preferred.

Epoxidation according to the invention is carried out at a temperature effective to achieve the desired olefin epoxidation, preferably at temperatures in the range of 0–250° C., more preferably, 20–100° C. The molar ratio of hydrogen to oxygen can usually be varied in the range of $H_2:O_2$=1:10 to 5:1 and is especially favorable at 1:5 to 2:1. The molar ratio of oxygen to olefin is usually 2:1 to 1:20, and preferably 1:1 to 1:10. A carrier gas may also be used in the epoxidation process. As the carrier gas, any desired inert gas can be used. The molar ratio of olefin to carrier gas is then usually in the range of 100:1 to 1:10 and especially 20:1 to 1:10.

As the inert gas carrier, noble gases such as helium, neon, and argon are suitable in addition to nitrogen and carbon dioxide. Saturated hydrocarbons with 1–8, especially 1–6, and preferably with 1–4 carbon atoms, e.g., methane, ethane, propane, and n-butane, are also suitable. Nitrogen and saturated $C_1$–$C_4$ hydrocarbons are the preferred inert carrier gases. Mixtures of the listed inert carrier gases can also be used.

Specifically in the epoxidation of propylene, propane can be supplied in such a way that, in the presence of an appropriate excess of carrier gas, the explosive limits of mixtures of propylene, propane, hydrogen, and oxygen are safely avoided and thus no explosive mixture can form in the reactor or in the feed and discharge lines.

The amount of catalyst used may be determined on the basis of the molar ratio of the titanium contained in the titanium zeolite to the olefin that is supplied per unit time. Typically, sufficient catalyst is present to provide a titanium/olefin per hour molar feed ratio of from 0.0001 to 0.1.

Depending on the olefin to be reacted, the epoxidation according to the invention can be carried out in the liquid phase, the gas phase, or in the supercritical phase. When a liquid reaction medium is used, the catalyst is preferably in the form of a suspension or fixed-bed. The process may be performed using a continuous flow, semi-batch or batch mode of operation.

If epoxidation is carried out in the liquid (or supercritical) phase, it is advantageous to work at a pressure of 1–100 bars and in the presence of one or more solvents. Suitable solvents include any chemical that is a liquid under reaction conditions, including, but not limited to, oxygenated hydrocarbons such as alcohols, ethers, esters, and ketones, aromatic and aliphatic hydrocarbons such as toluene and hexane, chlorinated aromatic and aliphatic hydrocarbons such as methylene chloride and chlorobenzene, supercritical $CO_2$, and water. Preferable solvents include water, supercritical $CO_2$, and oxygenated hydrocarbons such as alcohols, ethers, esters, ketones, and the like. Preferred oxygenated solvents include lower aliphatic $C_1$–$C_4$ alcohols such as methanol, ethanol, isopropanol, and tert-butanol, or mixtures thereof, and water. Fluorinated alcohols can be used. It is particularly preferable to use mixtures of the cited alcohols with water.

If epoxidation is carried out in the liquid (or supercritical) phase, it is advantageous to use a buffer. The buffer will typically be added to the solvent to form a buffer solution. The buffer solution is employed in the reaction to inhibit the formation of glycols or glycol ethers during epoxidation. Buffers are well known in the art.

Buffers useful in this invention include any suitable salts of oxyacids, the nature and proportions of which in the mixture, are such that the pH of their solutions may range from 3 to 10, preferably from 4 to 9 and more preferably from 5 to 8. Suitable salts of oxyacids contain an anion and cation. The anion portion of the salt may include anions such as phosphate, carbonate, bicarbonate, carboxylates (e.g., acetate, phthalate, and the like), citrate, borate, hydroxide, silicate, aluminosilicate, or the like. The cation portion of the salt may include cations such as ammonium, alkylammoniums (e.g., tetraalkylammoniums, pyridiniums, and the like), alkali metals, alkaline earth metals, or the like. Cation examples include $NH_4$, $NBu_4$, $NMe_4$, Li, Na, K, Cs, Mg, and Ca cations. More preferred buffers include alkali metal phosphate and ammonium phosphate buffers. Buffers may preferably contain a combination of more than one suitable salt. Typically, the concentration of buffer in the solvent is from about 0.0001 M to about 1 M, preferably from about 0.001 M to about 0.3 M. The buffer useful in this invention may also include the addition of ammonia gas to the reaction system.

The following examples merely illustrate the invention. Those skilled in the art will recognize many variations that are within the spirit of the invention and scope of the claims.

EXAMPLE 1

Catalyst Preparation

TS-1 can be made according to any known literature procedure. See, for example, U.S. Pat. No. 4,410,501, DiRenzo, et. al., *Microporous Materials* (1997), Vol. 10, 283, or Edler, et. al., *J. Chem. Soc., Chem. Comm.* (1995), 155.

Catalyst 1: TS-1 (a 1/16" extrudate: 80 wt. % TS1; 20 wt. % silica) is calcined in air at 550–600° C., and then recalcined at 350° C. for 8 hours. The calcined TS-1 (9.17 g) and deionized water (25 g) are added to a 100-mL round-bottom flask, then the pH of the solution is raised to 7.43 upon addition of a few drops of a 2.5 wt. % $NH_4OH$ solution. An aqueous solution of $(NH_3)_4Pd(NO_3)_2$ (0.1913 g of $(NH_3)_4Pd(NO_3)_2$ in 2.130 g of distilled water) is added to the flask over a three-minute period, while swirling the flask. The slurry is then placed on a rotovap at 30° C. and 30 rpm for 2 hours while the pH is adjusted every 15 minutes to about 7.5. The catalyst is then filtered and the solids are washed three times with deionized water before air drying overnight. The solids are dried in a vacuum oven at 81° C. for 4 hours, calcined in air at 300° C. for 8 hours, and then reduced in 5 vol. % hydrogen in nitrogen at 53° C. for 4 hours. Catalyst 1 contains 0.09 wt. % Pd.

EXAMPLE 2

Propylene Epoxidation Using CO Modifier

To evaluate the performance of the catalysts prepared in Example 1 in the presence of modifiers, the epoxidation of propylene using oxygen and hydrogen is carried out. The following procedure is employed.

Catalyst 1 (6.8 g) is added in layers, using quartz chips as a diluent, to a stainless steel Robinson-Mahoney basket. The entire basket is filled with the catalyst/quartz layers so that everything is held stationary in the basket.

The filled basket is inserted into a 500-cc stainless steel CSTR type reactor with an impeller running down the middle of the basket. Gas and liquid feeds enter the reactor, diffuse through the catalyst basket, and exit through two outlet filters. The reactor is electrically heated to 60–70° C. and pressurized to about 500 psig. An 80/20 methanol/water solvent is pumped through the reactor at about 2 mL/min along with a $(NH_4)H_2PO_4$ buffer (0.25 M aqueous solution) which was pumped at about 1 to 1.5 mL/hr. The gas flow rates were about 1500 to 3000 sccm (standard cubic centimeters per minute) of 5 vol. % oxygen in nitrogen, 15 to 40 g/hr propylene, 40–96 sccm hydrogen, and about 135 sccm of nitrogen. The CO is added in the range of 12 to 48 ppmv (part per million volume, as measure by the volume CO per total volume of propylene, oxygen, hydrogen, and nitrogen introduced into the reactor) using an auxiliary gas line. Propylene oxide and equivalents ("POE"), which include propylene oxide ("PO"), propylene glycol, and glycol ethers, are produced during the reaction.

A sharp drop in propane make is observed when CO is added but also a gradual decrease in catalyst productivity (POE yield) also occurs. Increasing temperature from 60° C. to 70° C. in addition to reducing the level of CO in the feed caused the POE yield to increase while still significantly decreasing propane make. See Table 1 for the results. The results indicate that an optimal POE yield with lower propane make may be possible by varying the temperature and the amount of added CO.

EXAMPLE 3

Propylene Epoxidation Studies with MA and PD Modifier

Example 2 is repeated with the exception that the basket reactor was empty of catalyst extrudate and quartz chips. Gas, liquid and buffer flows are similar to those described in Example 2. The reaction temperature is 60° C. and pressure is 500 psig. Initially, residual catalyst dust in the reactor produces a propane make of approximately 200 to 250 ppmv of the propylene in the feed. A gas mixture containing about 2000 ppmv of MA and 2000 ppmv of PD in nitrogen is then added to the feed gas at around 150 sccm flow rate. Following addition of the MA and PD mixture, propane make decreases by about 90% compared to results prior to addition of MA and PD. See Table 2 for the results. This experiment shows that MA and PD can effectively block the less desirable hydrogenation of propylene to propane.

TABLE 1

EFFECT OF CO ON PROPANE AND POE MAKE

| Reactor | Reactor Temp (° C.) | CO (ppmv) | Propylene (mole %) | Propane (ppmv) | Productivity[1] |
|---|---|---|---|---|---|
| Feed | 60 | 0 | 7.5 | 190 | — |
| Effluent | 60 | 0 | 7.5 | 1031–2300 | 0.14 |
| Feed | 60 | 48 | 7.1 | 190 | — |
| Effluent | 60 | 48 | 7.0 | 216 | 0.06 |
| Feed | 70 | 28 | 7.2 | 190 | — |
| Effluent | 70 | 28 | 7.2 | 490 | 0.1 |

TABLE 1-continued

EFFECT OF CO ON PROPANE AND POE MAKE

| Reactor | Reactor Temp (° C.) | CO (ppmv) | Propylene (mole %) | Propane (ppmv) | Productivity[1] |
|---|---|---|---|---|---|
| Feed | 70 | 14 | 7.2 | 190 | — |
| Effluent | 70 | 14 | 7.2 | 282–504 | 0.15 |

[1]Productivity = grams POE produced/gram of catalyst per hour.

TABLE 2

EFFECT OF MA AND PD ON PROPANE MAKE

| Reactor | MA + PD (ppmv) | Propylene (mole %) | Propane (ppmv) |
|---|---|---|---|
| Feed | 0 | 7.5 | 190 |
| Effluent | 0 | 7.5 | 431 |
| Feed | 305 | 7 | 190 |
| Effluent | 29 | 7 | 216 |

I claim:

1. A process for producing an epoxide comprising reacting an olefin, oxygen, and hydrogen in the presence of a noble metal-containing titanium or vanadium zeolite catalyst and a modifier selected from the group consisting of methylacetylene and propadiene.

2. The method of claim 1 wherein the noble metal-containing titanium or vanadium zeolite catalyst comprises titanium silicalite and palladium.

3. The method of claim 1 wherein the noble metal-containing titanium or vanadium zeolite catalyst comprises titanium silicalite, palladium, and one or more metals selected from the group consisting of gold and platinum.

4. The method of claim 1 wherein the noble metal-containing titanium or vanadium zeolite catalyst comprises a mixture of palladium-containing titanium or vanadium zeolite and palladium-free titanium or vanadium zeolite.

5. The process of claim 1 wherein the olefin is a $C_2$–$C_6$ olefin.

6. The process of claim 1 wherein the olefin is propylene.

7. The process of claim 1 wherein the modifier is a mixture of methylacetylene and propadiene.

8. The process of claim 1 further comprising a solvent selected from the group consisting of oxygenated hydrocarbons, aromatic and aliphatic hydrocarbons, chlorinated aromatic and aliphatic hydrocarbons, supercritical $CO_2$, and water.

9. The process of claim 1 further comprising a solvent selected from the group consisting of methanol, ethanol, isopropanol, and tert-butanol, and water.

10. A process for producing propylene oxide comprising reacting propylene, hydrogen and oxygen in a solvent in the presence of a palladium-containing titanium zeolite catalyst and a modifier selected from the group consisting of methylacetylene and propadiene.

11. The method of claim 10 wherein the palladium-containing titanium zeolite catalyst comprises titanium silicalite and palladium.

12. The method of claim 10 wherein the palladium-containing titanium zeolite catalyst comprises titanium silicalite, palladium, and one or more metals selected from the group consisting of gold and platinum.

13. The method of claim 10 wherein the palladium-containing titanium zeolite catalyst comprises a mixture of palladium-containing titanium zeolite and palladium-free titanium zeolite.

14. The process of claim 10 wherein the modifier is a mixture of methylacetylene and propadiene.

15. The process of claim 10 wherein the solvent is selected from the group consisting of oxygenated hydrocarbons, aromatic and aliphatic hydrocarbons, chlorinated aromatic and aliphatic hydrocarbons, supercritical $CO_2$, and water.

16. The process of claim 10 wherein the solvent is selected from the group consisting of methanol, ethanol, isopropanol, tert-butanol, and water.

* * * * *